US00PP16725P2

(12) United States Plant Patent

Staples et al.

(10) Patent No.: US PP16,725 P2
(45) Date of Patent: Jun. 27, 2006

(54) APPLE TREE NAMED 'RUBY PINK'

(50) Latin Name: *Malus domestica*
Varietal Denomination: Ruby Pink

(75) Inventors: Michael R. Staples, Red Hill South (AU); Jennifer R. Staples, Red Hill South (AU)

(73) Assignee: Tallawang Trust, Red Hill South (AU); Michael R. Staples and Jennifer R. Stamples, Trustees ( * ) Notice: Subject to any disclaimer, the term of this patent is extended or adjusted under 35 U.S.C. 154(b) by 145 days.

(21) Appl. No.: 10/855,876

(22) Filed: May 26, 2004

(51) Int. Cl.
*A01H 5/00* (2006.01)

(52) U.S. Cl. ..... Plt./161
(58) Field of Classification Search ..... Plt./161
See application file for complete search history.

(56) References Cited

U.S. PATENT DOCUMENTS

2003/0159188 P1 * 8/2003 McLean ..... Plt./161
2005/0120446 P1 * 6/2005 McLean ..... Plt./161

OTHER PUBLICATIONS http://www.affa.gov.au/content/pbr_database/plant_detail.cfm?AID=757211.*
UPOV ROM GTITM Computer Database, GTI Jouve Retrieval Software 2005/03 Citations for 'Ruby pink'.*

* cited by examiner

*Primary Examiner*—Kent Bell
*Assistant Examiner*—W. C. Haas
(74) *Attorney, Agent, or Firm*—Stratton Ballew PLLC

(57) ABSTRACT

Apple tree 'Ruby Pink' (*Malus domestica*) is a limb sport mutation of 'Cripps Pink' (U.S. Plant Pat. No. 7880). The fruit of 'Ruby Pink' is notable for its uniform ellipsoid shape, highly colored skin and firm flesh. 'Ruby Pink' is a late maturing variety, with harvest typically occurring after 'Cripps Pink.'

4 Drawing Sheets

Genus and species: *Malus domestica.*
Variety denomination: 'Ruby Pink'.

BACKGROUND OF THE INVENTION

The present invention relates to a new and distinct variety of apple tree named 'Ruby Pink,' which was discovered as a limb sport growing among a uniform block of 'Cripps Pink' (U.S. Plant Pat. No. 7,880) apple trees in a cultivated area of Main Ridge, Victoria, Australia. The limb sport mutation was discovered in May 1999 and progeny first asexually propagated in September 1999. Twenty-three trees on 'M26' rootstock were produced in 1999 with a further 400 produced via summer budding in February 2000. The original limb sport and progeny have been observed growing in a cultivated area of Red Hill South, Victoria, Australia, and the first observed fruiting of the propagated trees occurred in the 2001 season with mature fruit observed in May 2001.

BRIEF SUMMARY OF THE INVENTION

The 'Ruby Pink' variety is distinguished from 'Cripps Pink' and other apple varieties by the following unique combination of characteristics: the fruit is uniformly ellipsoid, as compared to the asymmetrical ellipsoid shape of 'Cripps Pink'; the fruit has a higher percentage of red color than 'Cripps Pink,' with fruit up to 100% red colored; the fruit matures later than 'Cripps Pink'; and the fruit has a higher firmness rating than 'Cripps Pink.'

Asexual reproduction of this new variety by grafting and budding onto rootstock shows that the foregoing and all other characteristics and distinctions come true to form and are established and transmitted through succeeding propagations.

BRIEF DESCRIPTION OF THE PHOTOGRAPHS

Figure 1:
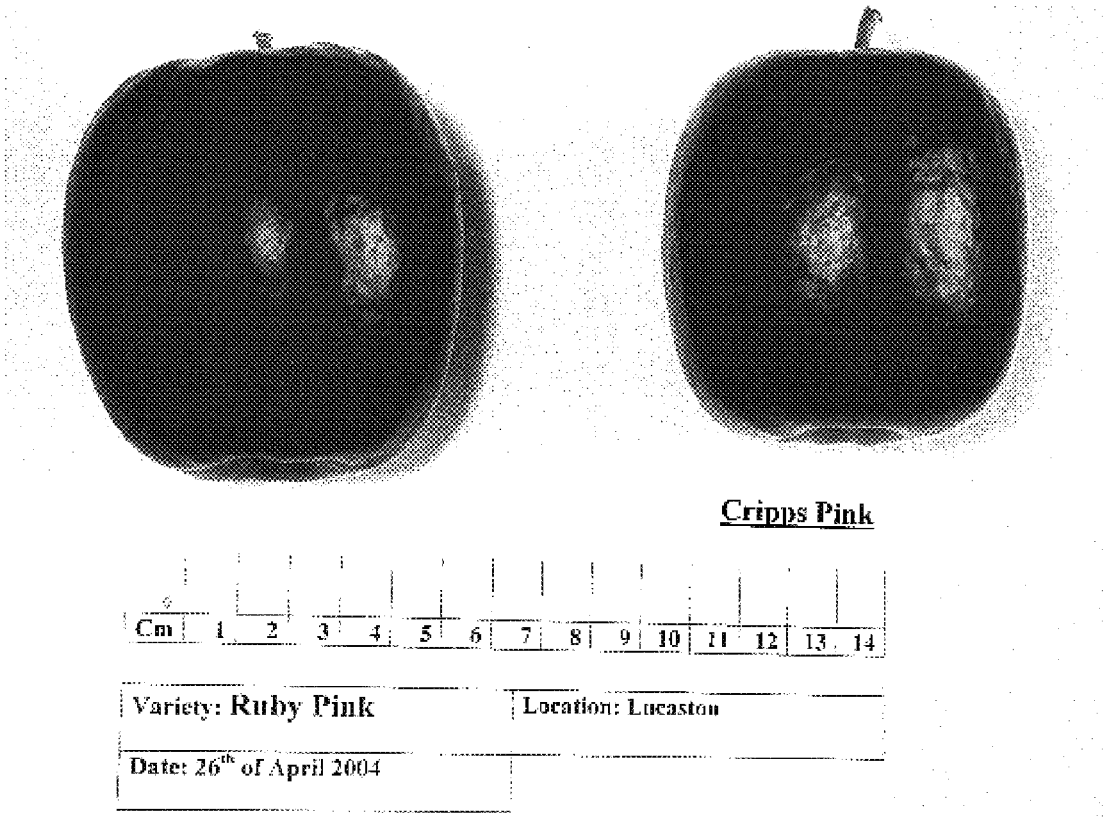
FIGS. 1 and 2 illustrate the distinctive color of 'Ruby Pink' apples, as compared to 'Cripps Pink' apples.
Figure 2:
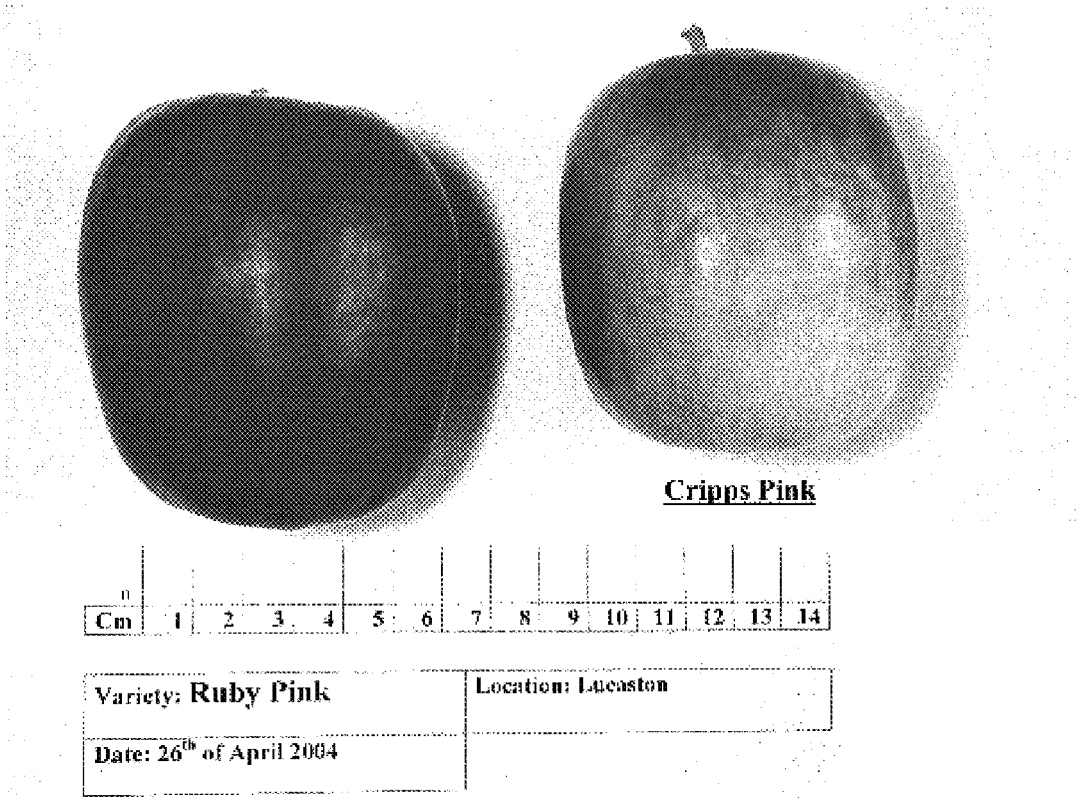
Figure 3:
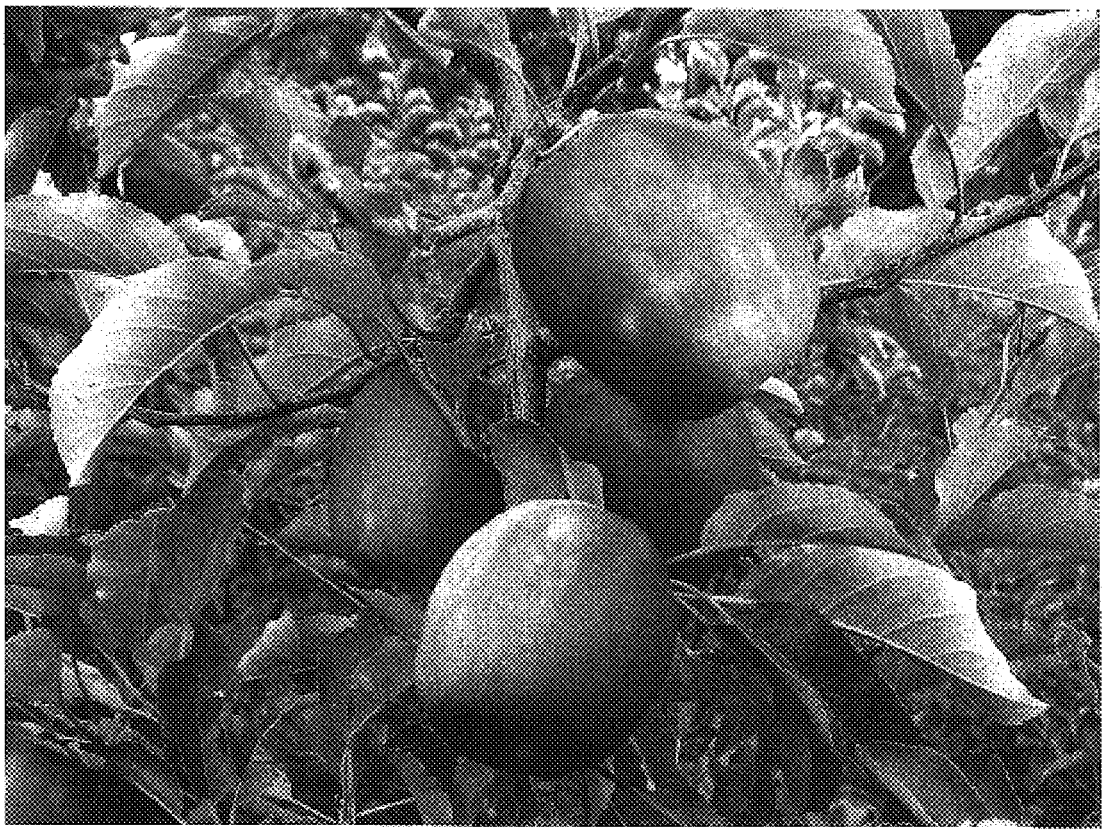
FIGS. 3 and 4 illustrate the fruit and branches of 'Ruby Pink'.
Figure 4:
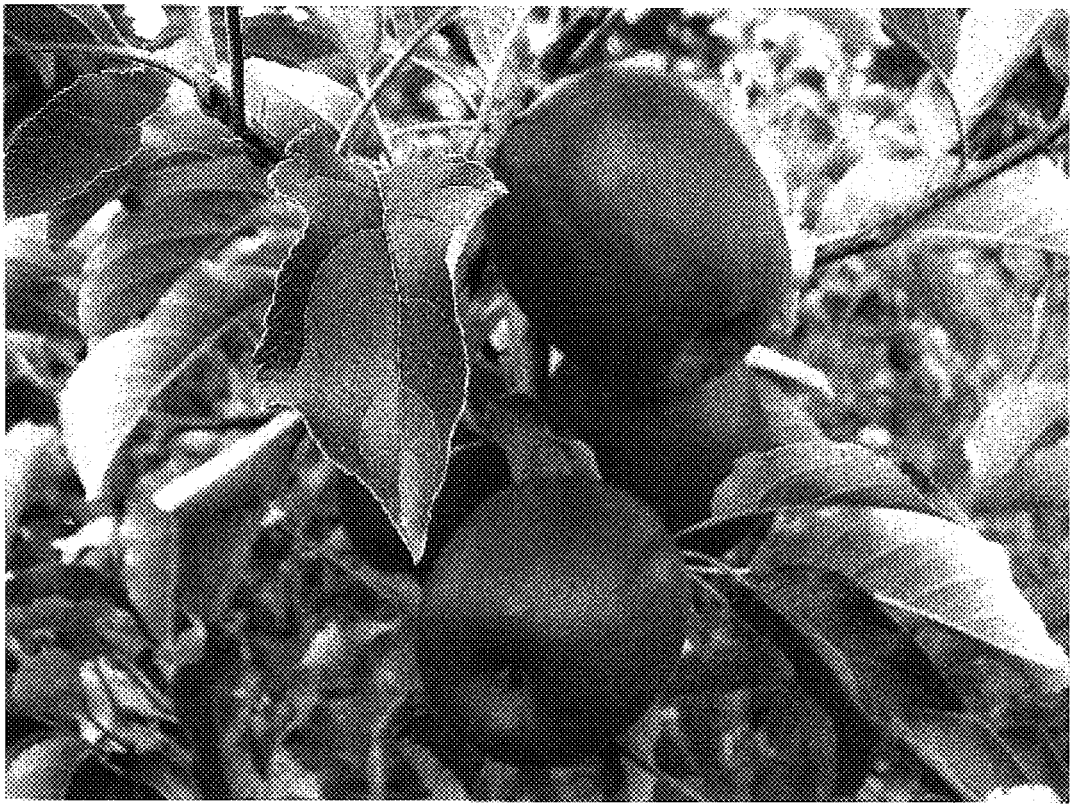

The colors of this illustration may vary with lighting conditions and, therefore, color characteristics of this new variety should be determined with reference to the observations described herein, rather than from these illustrations alone.

DETAILED BOTANICAL DESCRIPTION

The following detailed description of the 'Ruby Pink' variety is based on the originally identified tree and asexually reproduced progeny, grown on 'M26' rootstock, at Lucaston, Tasmania, Australia. Certain characteristics of this variety may change with changing environmental conditions (e.g., light, temperature, moisture), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. Color designations are made with reference to The Royal Horticultural Society (R.H.S.) Colour Chart.

Parentage: Limb sport mutation of 'Cripps Pink.'

Tree:

*Age of described tree.*—3 years.

*Vigor.*—Moderate.

*Overall shape.*—Upright spreading.

*Height.*—2.4 m.

*Width.*—0.8 m.

*Trunk.*—Medium Stocky; 25 mm at 300 mm above the ground, 100 mm above the graft union.

*Trunk bark texture.*—Smooth.

*Trunk bark color.*—Grey-Brown RHS N199A.

*Patches or other markings.*—White colored spots and scales, RHS N155B.

*Primary branches.*—Stout; branches emerge at an angle of about 60 to 90 degrees with branches higher in the tree emerging at approximately 60 degrees. Exemplary 2-year-old primary branches have been observed to have a caliper of about 9 mm measured at the base.

*Branch color.*—One-year old branches are Greyed-Purple RHS 183A, while older branches are Grey-Brown RHS 199B.

*Branch pubescence.*—Slight; White RHS 155A.

*Branch lenticels.*—Medium density, approximately 12 per square centimeter; Elongated; White RHS N155B; length 1 mm; width 0.5 mm.

*Internodes length* (*average, 1 year old shoot*).—3.5 cm.

*Bearing.*—Annual.

*Hardiness.*—Australian Zone hardy, comparable to 'Cripps Pink'.

*Drought, disease and insect resistance.*—Comparable to 'Cripps Pink'.

Leaves:

*Texture.*—Leathery.

*Sheen.*—Glossy.

*Length.*—About 9 cm to 10.5 cm; average 9.6 cm (average measurement from ten typical leaves).

*Width.*—About 4.8 cm to 6.4 cm; average 5.4 cm (average measurement from ten typical leaves).

*Petiole.*—Length 30 mm, diameter 1.8 mm; Greyed-Purple RHS 184A.

*Margin.*—Serrate.

*Tip shape.*—Acute.

*Stipules.*—Quantity 2; opposite, Yellow-Green RHS 147A; slender, length 10 mm to 16 mm.

*Leaf color.*—Upper leaf surface: Green RHS 147A. Lower leaf surface: Green RHS 146B. Vein: From Greyed-Purple RHS 184A at the base of the leaf to White RHS 155B at the apex.

*Pubescence.*—Light.

Flowers:

*Buds.*—Unopened — Length 15 to 20 mm, diameter 8 to 10 mm; Purple RHS 63A; Opened — Red-Purple RHS 69C.

*Size.*—Medium, 50 mm in diameter.

*Shape.*—Ovoid to round.

*Color.*—Upper petal surface: Red — Purple RHS 63A; Lower petal surface: Red-Purple RHS 69C.

*Petals.*—5 petals per flower; ovate; Length 22 mm, width 14 mm; petals not touching; margin smooth.

*Stamen.*—20 to 25 per flower; length 5 mm to 10 mm; arranged in a straight row; filaments Greyed-Green RHS 192D; anthers Yellow RHS 4C.

*Pistil.*—Stigma — length 10 mm; Styles — Quantity 5, fused at base, Yellow-Green RHS 144D.

*Sepals.*—5 per flower; length 8 mm, width 4 mm; Green RHS 144D tinged at the tip with Red-Purple RHS 59B; Arranged separately.

*Pollen.*—Yellow RHS 4C.

*Pollination requirements.*—There are no specific pollination requirements.

*Fragrance.*—Slight.

*Bloom season.*—In 2002 at Lucaston in Tasmania, Australia, blooming began on the $2^{nd}$ of October; full bloom on the $9^{th}$ of October; finishing on the $16^{th}$ of October.

Fruit:

*Size.*—Medium to large; Length 69 mm, width 71 mm (average of 10 typical 'Ruby Pink' apples).

*Shape.*—Asymmetrical, ellipsoid; ribbing is present; small lobes observed at calyx end.

*Cavity.*—Width 33 mm, depth 15 mm.

*Basin.*—Width 30 mm, depth 11 mm.

*Stem.*—Length 30 mm, diameter 2 mm; Greyed-Purple RHS 184A.

*Locules.*—5 open locules with seeds free of the carpel wall at maturity.

*Skin.*—Thin skin; glossy with a tendency to become waxy at maturity.

*Lenticels.*—Present but not conspicuous; diameter 5 mm, generally cream in color.

*Color.*—General color effect: Pink-Red RHS 46B. Ground color: Yellow-Green RHS 154C at maturity. Overcolor: Pink-Red RHS 46B. Russetting: Nil.

Ten typical apples of 'Ruby Pink' and 'Cripps Pink' cultivars from trees growing near to one another, were obtained on the $26^{th}$ of April 2004 and tested for certain properties. The average of these properties were as follows:

| | 'Ruby Pink' | 'Cripps Pink' |
|---|---|---|
| Firmness (pressure kg/cm$^2$) | 9.9 | 9.7 |
| Starch Index On Scale of 1 (high starch) to 6 (low starch) | 5.0 | 5.5 |
| Soluble Solids (in percent) | 13.3 | 14.4 |
| Red Color Rating On a scale of 1 (low) to 5 (high) | 4.5 | 3.5 |

*Flavor.*—Sub-acid to Sweet; about 13.5 to 15.5 Brix.

*Juiciness.*—Moderately juicy.

*Flavor.*—Full-bodied flavour.

*Flesh color.*—Yellow RHS 11D.

*Aroma.*—Moderate.

*Core.*—Generally round in shape; Diameter 30 mm; calyx tube closed; core lines defined.

*Seeds.*—About 1 to 2 seeds per cell; acute in shape; length 8.5 mm, width 5 mm; Greyed-Orange RHS 175A.

*Fruit production.*—First picking date in 2004 at Lucaston, Australia, was about 23 April; last picking date was about 3 May.

*Storage.*—Fruit remains fresh at room temperature for 7 days, and can be stored up to 6 months in cold storage (34° F.).

*Usage.*—Fresh eating.

It is claimed:

1. What is claimed is a new and distinct apple tree as herein shown and described.

* * * * *